United States Patent
Howell et al.

(10) Patent No.: US 10,178,965 B2
(45) Date of Patent: Jan. 15, 2019

(54) ACTIVITY MONITORING SYSTEM FOR PREGNANT WOMEN

(75) Inventors: Thomas A. Howell, Palo Alto, CA (US); Angeline Hadiwidjaja, Los Altos, CA (US); C. Douglass Thomas, Campbell, CA (US); Peter P. Tong, Mountain View, CA (US)

(73) Assignee: IpVenture, Inc., San Jose, CA (US)

( * ) Notice: Subject to any disclaimer, the term of this patent is extended or adjusted under 35 U.S.C. 154(b) by 2165 days.

(21) Appl. No.: 11/821,150

(22) Filed: Jun. 22, 2007

(65) Prior Publication Data

US 2008/0319353 A1    Dec. 25, 2008

(51) Int. Cl.
  *A61B 5/00*  (2006.01)
  *A61B 5/11*  (2006.01)

(52) U.S. Cl.
  CPC ............ *A61B 5/1118* (2013.01); *A61B 5/486* (2013.01); *A61B 5/4866* (2013.01)

(58) Field of Classification Search
  None
  See application file for complete search history.

(56) References Cited

U.S. PATENT DOCUMENTS

| | | | |
|---|---|---|---|
| 4,771,394 A * | 9/1988 | Cavanagh | A43B 3/0005 235/105 |
| 4,883,063 A | 11/1989 | Bernard et al. | |
| 4,931,046 A | 6/1990 | Newman | |
| 4,934,998 A | 6/1990 | Thomas, Jr. et al. | |
| 5,496,070 A * | 3/1996 | Thompson | 283/2 |
| 5,636,870 A * | 6/1997 | Enhorning | 283/2 |
| 5,749,372 A * | 5/1998 | Allen | A61B 5/486 482/8 |
| 5,913,834 A | 6/1999 | Francais | |
| 5,928,168 A * | 7/1999 | Laros, Jr. | 600/588 |
| 6,248,067 B1 | 6/2001 | Causey, III et al. | |
| 6,302,844 B1 | 10/2001 | Walker et al. | |
| 6,369,338 B1 * | 4/2002 | Kimura | G01G 19/4146 177/245 |
| 6,436,058 B1 | 8/2002 | Krahner et al. | |
| 6,443,890 B1 | 9/2002 | Schulze et al. | |
| 6,466,821 B1 | 10/2002 | Planca et al. | |
| 6,522,916 B1 * | 2/2003 | Kwon | 600/511 |

(Continued)

OTHER PUBLICATIONS

Basic Imaging-Ultrasound of Fetal Biometrics and Growth, Diagnostic and Interventional Radiology Department, Creighton University Medical Center, Omaha, Nebraska, http://radiology.creighton.edu/fetalbio.htm, downloaded Jun. 13, 2007, pp. 1-9.

(Continued)

*Primary Examiner* — Christopher A Flory
*Assistant Examiner* — Shirley Jian

(57) ABSTRACT

An activity feedback system for an individual is disclosed. The activity feedback system can be wearable by the individual and provide activity information and possibly other information to the individual. The individual can, for example, be a pregnant woman. The activity information can, for example, be used by a pregnant woman to monitor the amount of activity by the woman during as well as after her pregnancy. Besides activity information, the activity feedback system can also monitor, record or provide other information that is beneficial for individuals.

16 Claims, 9 Drawing Sheets

(56) References Cited

U.S. PATENT DOCUMENTS

| | | | |
|---|---|---|---|
| 6,569,094 B2 | 5/2003 | Suzuki et al. | |
| 6,602,469 B1 | 8/2003 | Maus et al. | |
| 6,610,012 B2 | 8/2003 | Mault | |
| 6,736,759 B1 | 5/2004 | Stubbs et al. | |
| 6,751,498 B1* | 6/2004 | Greenberg et al. | 600/511 |
| 6,898,550 B1 | 5/2005 | Blackadar et al. | |
| 7,072,791 B2* | 7/2006 | Harima | A61B 5/4866 |
| | | | 702/160 |
| 7,195,600 B2* | 3/2007 | Ueda | G06F 19/3475 |
| | | | 600/547 |
| 7,228,295 B2* | 6/2007 | Lapointe et al. | 706/21 |
| 7,255,437 B2 | 8/2007 | Howell et al. | |
| 7,296,733 B2* | 11/2007 | Nguyen | 235/1 R |
| 7,323,141 B2 | 1/2008 | Kirchhevel et al. | |
| 7,333,850 B2* | 2/2008 | Marossero | A61B 5/02411 |
| | | | 600/511 |
| 7,402,135 B2 | 7/2008 | Leveque et al. | |
| 7,953,613 B2* | 5/2011 | Gizewski | G06F 19/345 |
| | | | 705/2 |
| 8,221,290 B2* | 7/2012 | Vincent | A63B 24/0021 |
| | | | 273/440 |
| 8,360,904 B2* | 1/2013 | Oleson | A63B 24/0062 |
| | | | 463/36 |
| 8,386,008 B2* | 2/2013 | Yuen | A61B 5/0002 |
| | | | 600/382 |
| 8,702,430 B2* | 4/2014 | Dibenedetto | G06F 19/3418 |
| | | | 434/247 |
| 9,585,614 B2* | 3/2017 | Dugan | A61B 5/0077 |
| 9,629,558 B2* | 4/2017 | Yuen | A61B 5/0205 |
| 2002/0028995 A1* | 3/2002 | Mault | 600/437 |
| 2002/0062225 A1 | 5/2002 | Siperco | |
| 2002/0082480 A1 | 6/2002 | Riff et al. | |
| 2002/0147617 A1 | 10/2002 | Schoenbaum et al. | |
| 2003/0062046 A1 | 4/2003 | Wiesmann et al. | |
| 2003/0065257 A1 | 4/2003 | Mault et al. | |
| 2003/0179094 A1* | 9/2003 | Abreu | 340/573.1 |
| 2003/0204132 A1 | 10/2003 | Suzuki et al. | |
| 2003/0208108 A1 | 11/2003 | Shewmake et al. | |
| 2003/0208113 A1* | 11/2003 | Mault et al. | 600/316 |
| 2003/0211007 A1 | 11/2003 | Maus et al. | |
| 2003/0212575 A1* | 11/2003 | Saalsaa et al. | 705/2 |
| 2004/0034284 A1 | 2/2004 | Aversano et al. | |
| 2004/0037738 A1 | 2/2004 | Maus et al. | |
| 2004/0038389 A1 | 2/2004 | Maus et al. | |
| 2004/0049355 A1 | 3/2004 | Maus et al. | |
| 2004/0087840 A1* | 5/2004 | Main | 600/304 |
| 2004/0122706 A1 | 6/2004 | Walker et al. | |
| 2004/0133081 A1 | 7/2004 | Teller et al. | |
| 2004/0204959 A1 | 10/2004 | Moreano et al. | |
| 2004/0243020 A1* | 12/2004 | Ueda | A61B 5/0537 |
| | | | 600/547 |
| 2004/0249672 A1 | 12/2004 | Bocionek et al. | |
| 2005/0020888 A1* | 1/2005 | Harima | A61B 5/4866 |
| | | | 600/300 |
| 2005/0021370 A1 | 1/2005 | Riff et al. | |
| 2005/0022817 A1 | 2/2005 | Alvey | |
| 2005/0027562 A1 | 2/2005 | Brown | |
| 2005/0038344 A1 | 2/2005 | Chance | |
| 2005/0085742 A1* | 4/2005 | Ueda | A61B 5/0537 |
| | | | 600/547 |
| 2005/0113650 A1* | 5/2005 | Pacione et al. | 600/300 |
| 2005/0177059 A1* | 8/2005 | Koivumaa | A61B 5/0488 |
| | | | 600/546 |
| 2005/0228692 A1 | 10/2005 | Hodgdon | |
| 2005/0267377 A1* | 12/2005 | Marossero et al. | 600/511 |
| 2006/0122468 A1* | 6/2006 | Tavor | G06F 19/3475 |
| | | | 600/300 |
| 2006/0167373 A1* | 7/2006 | Takehara | A61B 5/0537 |
| | | | 600/547 |
| 2006/0217630 A1* | 9/2006 | Ueda | G06F 19/3475 |
| | | | 600/547 |
| 2006/0231109 A1 | 10/2006 | Howell et al. | |
| 2006/0241355 A1 | 10/2006 | Howell et al. | |
| 2006/0248946 A1 | 11/2006 | Howell et al. | |
| 2007/0022578 A1 | 2/2007 | Crockett, IV et al. | |
| 2007/0024465 A1 | 2/2007 | Howell et al. | |
| 2007/0048224 A1 | 3/2007 | Howell et al. | |
| 2007/0102503 A1* | 5/2007 | Nguyen | A61B 5/1118 |
| | | | 235/1 R |
| 2007/0167753 A1 | 7/2007 | Van Wyk et al. | |
| 2007/0255122 A1* | 11/2007 | Vol et al. | 600/301 |
| 2008/0004904 A1* | 1/2008 | Tran | 705/2 |
| 2008/0068559 A1 | 3/2008 | Howell et al. | |
| 2008/0146890 A1* | 6/2008 | LeBoeuf et al. | 600/300 |
| 2008/0167553 A1* | 7/2008 | Paltieli et al. | 600/437 |
| 2008/0183287 A1 | 7/2008 | Ayre | |
| 2009/0012432 A1* | 1/2009 | Sharf | 600/588 |
| 2009/0024004 A1* | 1/2009 | Yang | 600/301 |
| 2009/0308742 A1* | 12/2009 | Paranjape | 204/403.1 |
| 2010/0274100 A1* | 10/2010 | Behar et al. | 600/301 |
| 2012/0083669 A1* | 4/2012 | Abujbara | G06F 19/3475 |
| | | | 600/300 |
| 2012/0083705 A1* | 4/2012 | Yuen | A61B 5/0002 |
| | | | 600/508 |
| 2013/0158366 A1* | 6/2013 | Bogineni | A61B 5/0002 |
| | | | 600/301 |
| 2015/0289822 A1* | 10/2015 | Dugan | A61B 5/0077 |
| | | | 600/301 |
| 2015/0305668 A1* | 10/2015 | Dugan | A61B 5/0077 |
| | | | 600/301 |
| 2016/0374608 A1* | 12/2016 | Dugan | A61B 5/6831 |
| | | | 600/301 |

OTHER PUBLICATIONS

FitSense Technology, Inc., FS-1 Frequently Asked Questions, http://www.fitsense.com/FS1FAQ.aspx, downloaded Apr. 23, 2006, 2 pages.

FitSense Technology, Inc., FS-1 Speedometer, Athlete's Manual, version 2.0 Jul. 2, 2001, 32 pages.

FitSense Technology, Inc., ActiHealth Intelligent Health Network, downloaded Apr. 23, 2006, 1 page.

FitSense Technology, Inc., ActiHealth Personal Monitoring System, http://www.fitsense.com/SystemDevice.aspx, downloaded Apr. 23, 2006, 2 pages.

FitSense Technology, Inc., BodyLan, Ultra Low-Power Wireless Personal Area Network, http://www.fitsense.com/Wireless.aspx, downloaded Apr. 23, 2006, 1 page.

FitSense Technology, Inc., FitSense FS-1 Speedometer, http://www.fitsense.com/FS1.aspx, downloaded Apr. 23, 2006, 2 pages.

FitSense Technology, Inc., Health & Wellness Program Providers, Personalized monitoring & feedback tools, http://www.fitsense.com/HealthWellness.aspx, downloaded Apr. 23, 2006, 1 page.

FitSense Technology, Inc., Health Coaches & Disease Management Providers, Personalized monitoring & feedback tools, http://www.fitsense.com/DiseaseManagement.aspx, downloaded Apr. 23, 2006, 1 page.

LifePoint Inc.—Saliva Based Testing Systems for the next generation, LifePoint® IMPACT® Test System, undated, 2 pages.

Mirkin, Gabe M.D., "Recovery Pulse Rate: Heart Attack?," http://www.drmirkin.com/heart/8076.html, Oct. 28, 1999, 1 page.

NELLCOR™ Oximax Sensors™, Tyco Healthcare Group, 2002, pp. 1-5.

Nellcor OxiMax, Sensor Selection Guide, Tyco Healthcare, Oct. 2002, 12 pages.

Nonin OEM III Module, Internal Oximetry, Nonin Medical, Inc., http://www.nonin.com/products/oem/oem3module.asp, downloaded Jul. 18, 2006, pp. 1-2.

Nonin Oem III Module, Module, Specifications, Nonin Medical, Inc., copyright 2005, pp. 1-11.

OEM Oximetry Development Kit Order Form, Nonin Medical, Inc., 1 pg.

ViOptix :: Technology, "How ODIS Works," copyright 2006, ViOptix, Inc., http://www.vioptix.com/docs/technology/howitworks.asp, downloaded Nov. 29, 2006, pp. 1-2.

U.S. Appl. No. 11/314,545, filed Dec. 20, 2005.

U.S. Appl. No. 11/888,723, filed Sep. 2, 2007.

(56) References Cited

OTHER PUBLICATIONS

*Moritex USA Incorporated, Sensors & Meters, copyright 2004, tp://www.moritexusa.com/products/product_category.php?plid=5&pcid=10, downloaded Apr. 19, 2006, pp. 1-2.

Basic Imaging > Ultrasound of Fetal Biometrics and Growth, Creighton University Medical Center, Diagnostic and Interventional Radiology Department, http://radiology.creighton.edu/fetalbio.htm, downloaded Nov. 6, 2007, pp. 1-12.

Freudenrich, Craig, "How Prenatal Testing Works", HowStuffWorks, Inc., downloaded Mar. 23, 2007, pp. 1-11.

Hepper, Peter and B Sara Shahidullah, "Development of Fetal Hearing", May 24, 1994. Archives of Disease in Childhood. 71: F81-F87.

Inventory of Medical and Laboratory Equipment—Foremost Equipment, fetal monitors, http://www.foremostequipment.com/quick_search.asp?type_search=24&switch=1, downloaded Sep. 15, 2006, 2 pages.

Moritex USA Incorporated, Sensors & Meters, copyright 2004, http://www.moritexusa.com/products/product_category.php?plid=5&pcid=10, downloaded Apr. 19, 2006, pp. 1-2.

RemindHer, NVOrganon, http://www.contraception.net, 2004, pp. 1-2.

Sorbero et al. Assessment of Pay-for-Performance Options for Medicare Physician Services: Final Report. RAND Health. May 2006.

Basic Imaging > Ultrasound of Fetal Biometrics and Growth, Creighton University Medical Center, Diagnostic and Interventional Radiology Department, http://radiology.creighton.edu/fetalbio.htm, downloaded Nov. 6, 2007, pp. 1-9.

* cited by examiner

ACTIVITY MONITORING SYSTEM FOR PREGNANT WOMEN

CROSS-REFERENCE TO RELATED APPLICATIONS

This application references the following applications: (i) U.S. patent application Ser. No. 11/314,545, filed Dec. 20, 2005, entitled "BOTTLE OF LOTION WITH A SENSOR," and which is hereby incorporated herein by reference; (ii) U.S. patent application Ser. No. 11/451,781, filed Jun. 12, 2006, entitled "PERSONAL AND PORTABLE BOTTLE," and which is hereby incorporated herein by reference; (iii) U.S. patent application Ser. No. 11/451,780, filed Jun. 12, 2006, entitled "HEALTHCARE BASE," and which is hereby incorporated herein by reference; (iv) U.S. patent application Ser. No. 11/479,665, filed Jun. 30, 2006, entitled "MOISTURE SENSOR FOR SKIN," and which is hereby incorporated herein by reference; (v) U.S. patent application Ser. No. 11/491,774, filed Jul. 22, 2006, entitled "PORTABLE CONTAINER WITH SPEAKER ATTACHED," and which is hereby incorporated herein by reference; (vi) U.S. patent application Ser. No. 11/592,431, filed Nov. 2, 2006, entitled "METHOD AND APPARATUS TO SENSE HYDRATION LEVEL OF A PERSON," and which is hereby incorporated herein by reference; (vii) U.S. patent application Ser. No. 11/725,360, filed Mar. 17, 2007, entitled "MEDICAL MONITORING SYSTEM," and which is hereby incorporated herein by reference; (viii) U.S. Provisional Patent Application No. 60/636,969, filed Dec. 20, 2004, entitled "PREVENTIVE MEDICAL SYSTEMS, METHODS AND APPARATUS," and which is hereby incorporated herein by reference; (ix) U.S. Provisional Patent Application No. 60/652,213, filed Feb. 14, 2005, entitled "PREVENTIVE MEDICAL SYSTEMS, METHODS AND APPARATUS," and which is hereby incorporated herein by reference; (x) U.S. Provisional Patent Application No. 60/670,957, filed Apr. 13, 2005, entitled "BOTTLE OF LOTION WITH A LOTION SENSOR," and which is hereby incorporated herein by reference; (xi) U.S. Provisional Patent Application No. 60/689,312, filed Jun. 10, 2005, entitled "PERSONAL AND PORTABLE BOTTLE," and which is hereby incorporated herein by reference; (xii) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference; (xiii) U.S. Provisional Patent Application No. 60/785,825, filed Mar. 24, 2006, and entitled "MEDICAL MONITORING SYSTEM," which is hereby incorporated herein by reference; and (xiv) U.S. Provisional Patent Application No. 60/880,308, filed Jan. 12, 2007, entitled "PORTABLE PRESSURE SENSOR AND HEART-BEAT SENSOR FOR PREGNANCY," and which is hereby incorporated herein by reference.

BACKGROUND OF THE INVENTION

Today, pedometers are available for general usage to monitor distance or steps traveled. A user can clip a pedometer onto his belt when monitoring distance or steps traveled, such as during walking or running.

SUMMARY OF THE INVENTION

Various embodiments of the invention pertains to an activity feedback system for an individual. The activity feedback system can be wearable by the individual and provide activity information and possibly other information to the individual. The individual can, for example, be a pregnant woman. The activity information can, for example, be used by a pregnant woman to monitor the amount of activity by the woman during as well as after her pregnancy. Besides activity information, the activity feedback system can also monitor, record or provide other information that is beneficial for individuals.

The invention can be implemented in numerous ways, including as a system, device, apparatus, and method. Several embodiments of the invention are discussed below.

As a wearable electronic device, one embodiment of the invention includes at least: a housing having a display and at least one input mechanism; an activity monitor configured to monitor activity of a user of said wearable electronic device; a memory device for storage of information related to the activity of the user and a due date associated with the user; a processor operatively connected to said input mechanism, said activity monitor and said memory device, said processor being configured to compare information related to the activity of the user with at least one threshold level that is dependent on the due date associated with the user; and an output mechanism operatively connected to said processor, said output mechanism being configured to operate to output activity feedback to the user of said wearable electronic device.

As a method for operating a wearable electronic device to provide activity information to a pregnant person, one embodiment of the invention includes at least: receiving activity data related to the user; obtaining due date associated with the user; determining at least one threshold level based on the due date; and outputting activity feedback based on the activity data and the threshold level.

Other aspects and advantages of the invention will become apparent from the following detailed description taken in conjunction with the accompanying drawings which illustrate, by way of example, the principles of the invention.

BRIEF DESCRIPTION OF THE DRAWINGS

Embodiments of the invention will be readily understood by the following detailed description in conjunction with the accompanying drawings, wherein like reference numerals designate like structural elements, and in which.

DETAILED DESCRIPTION OF THE INVENTION

Various embodiments of the invention pertain to an activity feedback system for an individual. The activity feedback system can be wearable by the individual and provide activity information and possibly other information to the individual. The individual can, for example, be a pregnant woman. The activity information can, for example, be used by a pregnant woman to monitor the amount of activity by the woman during as well as after her pregnancy. Besides activity information, the activity feedback system can also monitor, record or provide other information that is beneficial for individuals.

Women who become pregnant have many concerns. One concern is whether they are properly active. If a pregnant woman does not remain sufficiently active, there can be undesired health issues. For example, when a pregnant women is stationary for too long, the lack of activity can lead to reduced circulation, swollen legs, back aches, etc. Consequently, pregnant women need to be concerned with their activity over the course of their pregnancy. Unfortunately, conventional pedometers are unable to adequately assist pregnant women to manage their activity. Thus, there is a need for improved approaches and devices that assist pregnant women in managing their activity during pregnancy.

Embodiments of the invention are discussed below with reference to FIGS. 1-7C. However, those skilled in the art will readily appreciate that the detailed description given herein with respect to these figures is for explanatory purposes as the invention extends beyond these limited embodiments.

Figure 1:
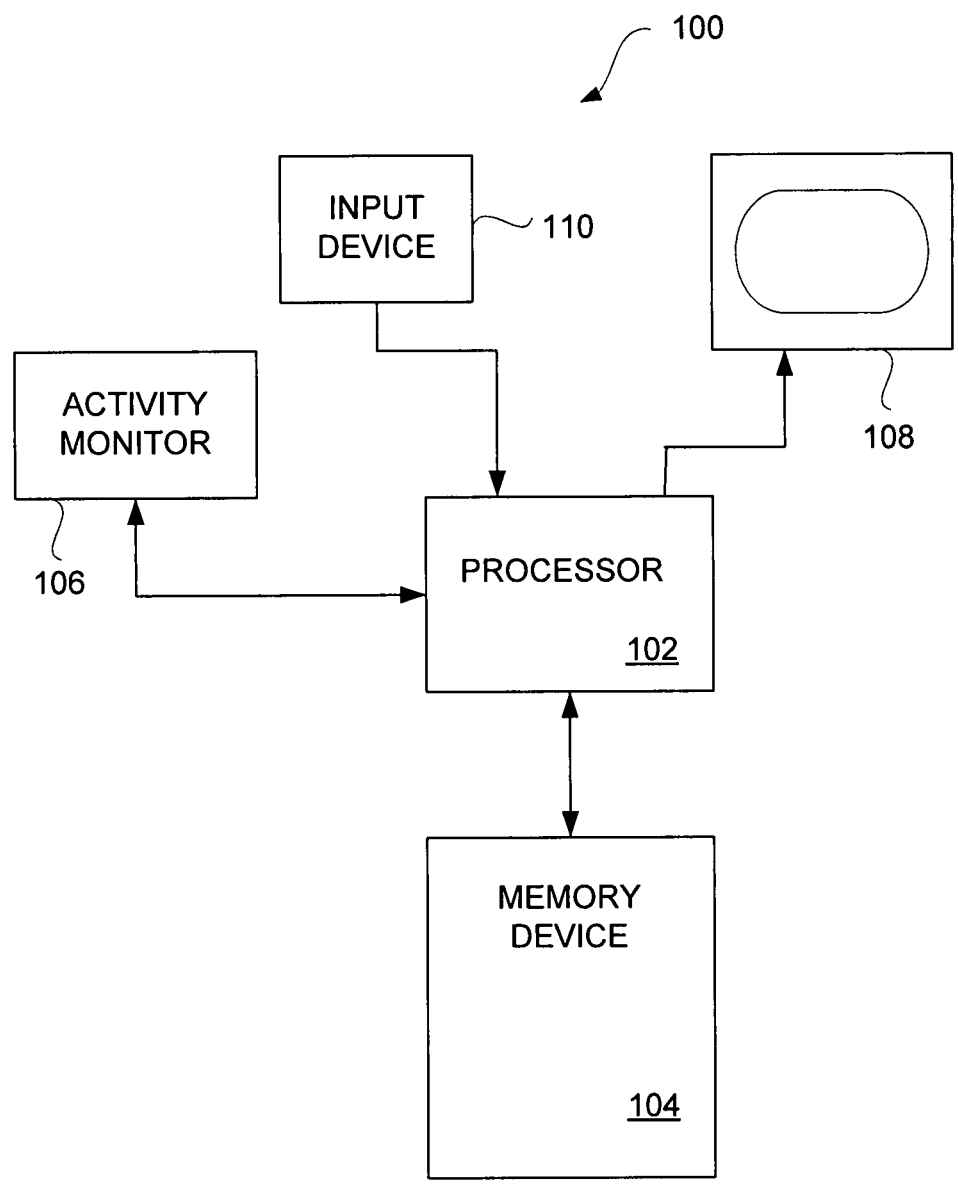
FIG. 1 is a block diagram of a wearable electronic device according to one embodiment of the invention.

FIG. 1 is a block diagram of a wearable electronic device 100 according to one embodiment of the invention. The wearable electronic device 100 includes a processor 102 that controls the overall operation of the wearable electronic device 100. In addition, the wearable electronic device 100 includes a memory device 104, an activity monitor 106, an output mechanism 108 (or output device), and an input mechanism 110 (or input device). The processor 102 can interact any of the memory device 104, the activity monitor 106, the output mechanism 108 and the input mechanism 110. The memory device 104 can store program instructions and/or data to be utilized by the processor 102 that controls operation of the wearable electronic device 100.

The activity monitor 106 monitors the activity associated with the wearable electronic device 100. The activity of the wearable electronic device 100 can be commensurate with the activity of a user that wears the wearable electronic device 100. In one embodiment, the activity monitor 106 can, for example, include an accelerometer. In another embodiment, the activity monitor 106 can, for example, include a pedometer. More generally, the activity monitor 106 can be mechanical, electrical or electro-mechanical. Typically, the processor 102 will receive activity data provided by the activity monitor 106. The processor 102 can then process the activity data to produce output data that can be not only stored in the memory device 104 but also output (e.g., typically in a user-friendly manner) via the output mechanism 108. In one embodiment, the output data includes processed activity data. For example, when the output mechanism 108 is a display device, the processed activity information can be displayed on the display device.

The wearable electronic device 100 is particularly useful for pregnant women. In particular, a pregnant woman should exercise (i.e., be active) in a controlled fashion during her pregnancy. The amount of recommended exercise can vary depending upon the person and the stage of pregnancy.

The input mechanism 110 of the wearable electronic device 100 can enable a user of the wearable electronic device 100 to input data into the wearable electronic device 100. Input data that is input via the input mechanism 110 can be received by the processor 102 and stored in the memory device 104. Examples of data that can be input to the wearable electronic device 100 can be numerous. One example of data that can be input is pregnancy data, such as estimated due date (or estimated delivery date). Another example of data that can be input is user personalization data, such as one or more of: pre-pregnancy activity information, doctor information, health information, appointments, contact information, baby name(s), etc. The input data can also be stored in the memory device 104.

According to one embodiment of the invention, the wearable electronic device 100 provides its user with activity feedback during her pregnancy. The amount of activity that is appropriate for the pregnant woman will normally vary depending upon her proximity to the due date. The processor 102 can personalize its activity feedback to the user based on estimated due date and/or personalization information. The personalization information can, for example, include prior activity information.

The activity feedback provided to the user can be presented in various different ways. In one example, the activity feedback can be presented as a visual indication of a distance (e.g., miles or meters) or number of steps. The distance or steps can be accumulated over a period of time, such as daily or weekly. A history of the activity feedback can also be made available. The activity feedback can be provided with reference to recommended or target activity levels. The activity feedback can also be provided with respect to a suggested activity range.

Figure 2:
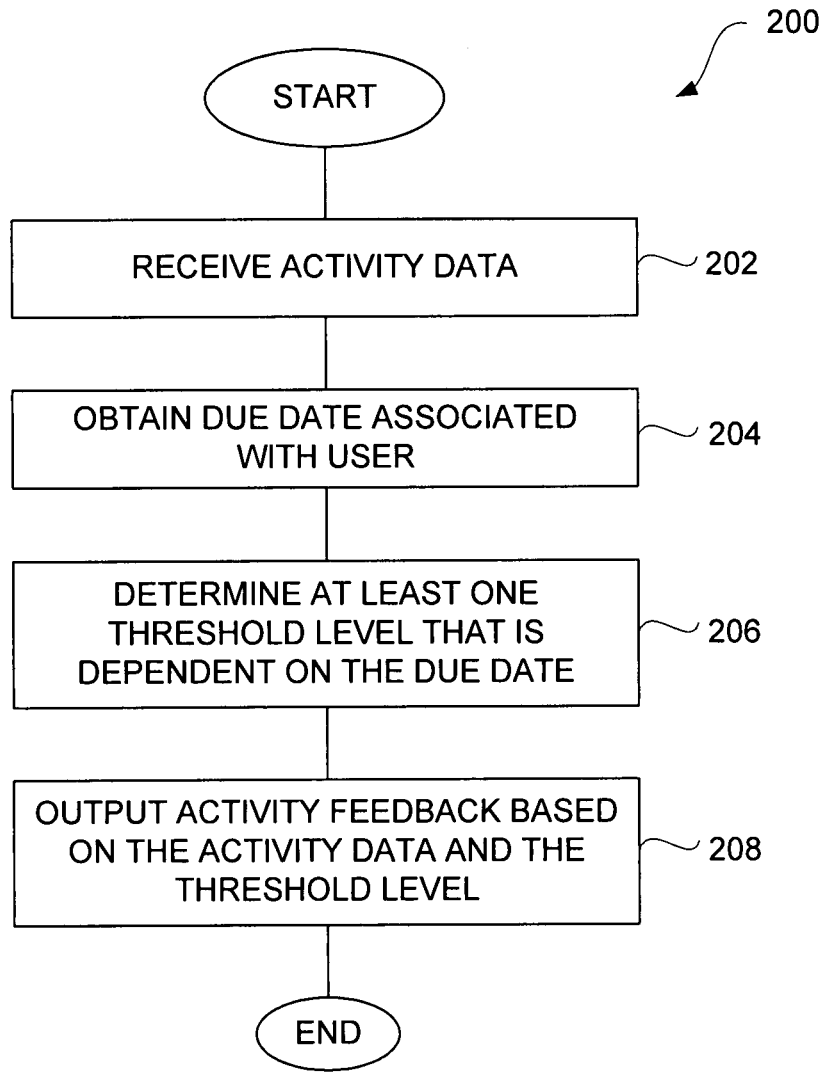
FIG. 2 is a flow diagram of an activity feedback process according to one embodiment of the invention.

FIG. 2 is a flow diagram of an activity feedback process 200 according to one embodiment of the invention. The activity feedback process 200 is, for example, performed by the wearable electronic device 100 illustrated in FIG. 1, such as the processor 102 illustrated in FIG. 1.

The activity feedback process 200 can receive 202 activity data. A due date associated with the user can also be obtained 204. The due date can be obtained from the user, from a doctor associated with the user, or from some third party. The due date can be input by user interaction with the input mechanism 110. Alternatively, the due date can be input to the wearable electronic device via a network (by a wired connection or by a wireless connection).

Next, at least one threshold level is determined 206 dependent upon the due date. After the at least one threshold level has been determined 206, activity feedback based on the activity data and the threshold level can be output 208. The activity feedback can, for example, be output 208 by displaying such feedback on a display device. In this case, the activity feedback can include text and/or graphical elements that are displayed (i.e., visual output) on a display device. Alternatively, the activity feedback can be output 208 in an audio fashion. After the activity feedback has been output 208, the activity feedback process 200 can end.

Figure 3:
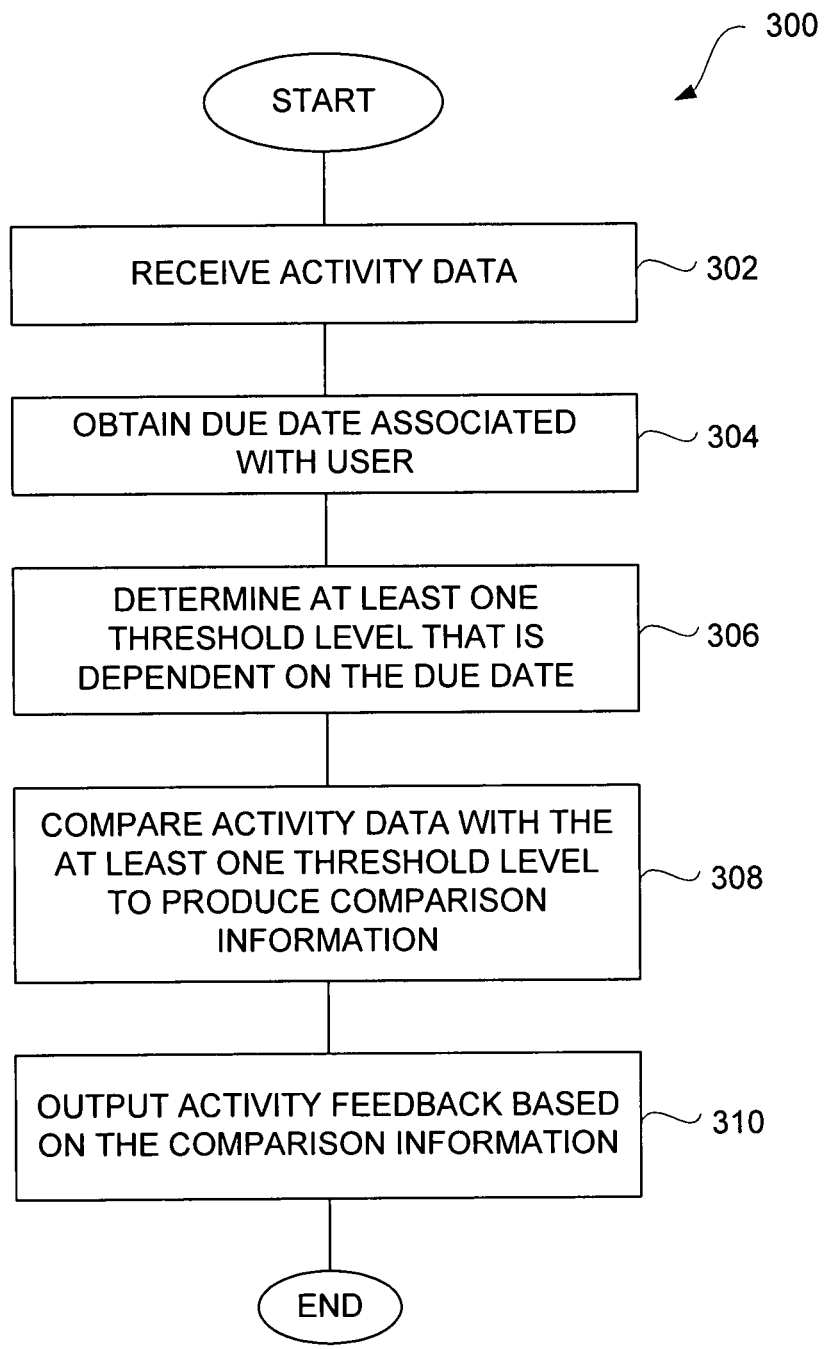
FIG. 3 is a flow diagram of an activity feedback process according to another embodiment of the invention.

FIG. 3 is a flow diagram of an activity feedback process 300 according to another embodiment of the invention. The activity feedback process 300 is, for example, performed by the wearable electronic device 100 illustrated in FIG. 1.

The activity feedback process 300 initially receives 302 activity data. For example, the activity data can be provided by the activity monitor 106 illustrated in FIG. 1. Next, a due data associated with the user is obtained 304. The due date associated with the user can be obtained 304 from data storage, such as the memory device 104, or from a user of the wearable electronic device 100 via the input mechanism 110. In this regard, the user can be the pregnant woman, a doctor, or some other third party that is utilizing the wearable electronic device 100.

Next, at least one threshold level is determined 306 dependent upon the due date. In other words, according to one embodiment, the threshold level varies depending upon the due date. Thereafter, the activity data can be compared 308 with the at least one threshold level to produce comparison information. Activity feedback can then be output 310 based on the comparison information. Following the block 310, the activity feedback process 300 can end.

As noted above, the activity feedback process 200 and the activity feedback process 300 can utilize one or more threshold levels. The threshold levels can be dependent on due date, doctor or other health provider input, user characteristics, etc.

In one embodiment, one or more threshold levels utilized in evaluating activity data in order to produce activity feedback are selected dependent upon the due date associated with the user. The due date can be represented as a number of days to go ("days to go"). The due date can be input to the wearable electronic device by a user directly, such as by entering a due date, or indirectly, such as by entry of a conception date or other information (e.g., menstrual cycle) suitable for establishing a conception date.

In one embodiment, a doctor can interact with the wearable electronic device to influence the one or more threshold levels utilized in evaluating activity data pertaining to the user. For example, a doctor (or another person at the doctor's instructions) can interact with a user input mechanism of the wearable electronic device to alter the threshold levels. As another example, a doctor (or another person at the doctor's instructions) can interact with a user input mechanism of another computing device that communicates with the wearable electronic in a wired or wireless manner. In one exemplary scenario, the doctor desires that the activity thresholds for the user be reduced so that premature delivery does not result. The one or more threshold levels still can be dependent on the due date associated with the user.

In one embodiment, user characteristics associated with a user can be used to influence the one or more threshold levels utilized in evaluating activity data pertaining to the user. As an example, the user characteristics can pertain to one or more of weight, age, health, or physical condition. These user characteristics can be stored in the wearable electronic device. One or more of these user characteristics can be monitored over time and stored as historical data.

In one embodiment, electronic devices (e.g., sensors) can be used to influence the one or more threshold levels utilized in evaluating activity data pertaining to the user.

Figure 4A:
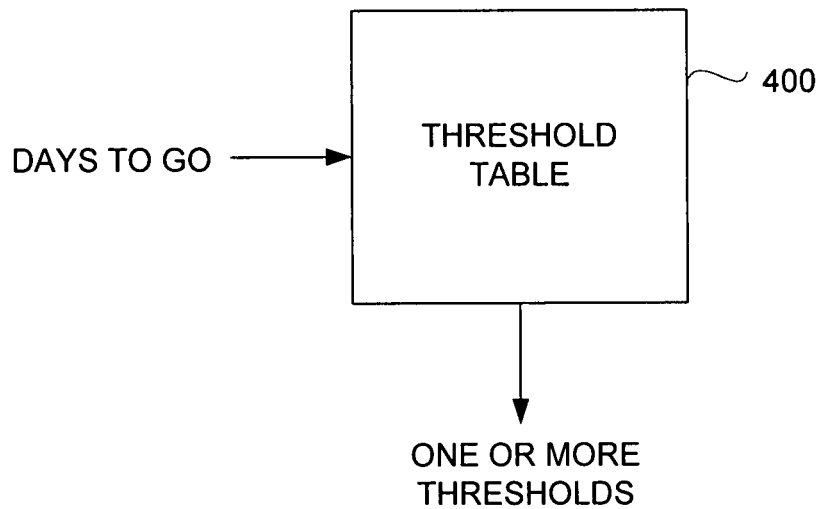
FIG. 4A is a block diagram of a threshold table according to one embodiment of the invention.

FIG. 4A is a block diagram of a threshold table 400 according to one embodiment of the invention. The threshold table 400 is a data structure that can be accessed to determine one or more threshold levels. In this embodiment, the threshold table 400 is accessed using a number, such as a number of days to go. With such an input, the threshold table 400 outputs one or more thresholds that are suitable for use given the number of days to go. Accordingly, as the number of days to go decreases, the one or more thresholds being utilized can dynamically change. The ability to dynamically change the thresholds based on the number of days to go is advantageous because activity associated with a pregnant woman should vary dependent upon the number of days to go. In particular, as the number of days to go gets relatively small, the amount of activity should be substantially decreased as compared to the activity level when the number of days to go is several months or more.

Figure 4B:
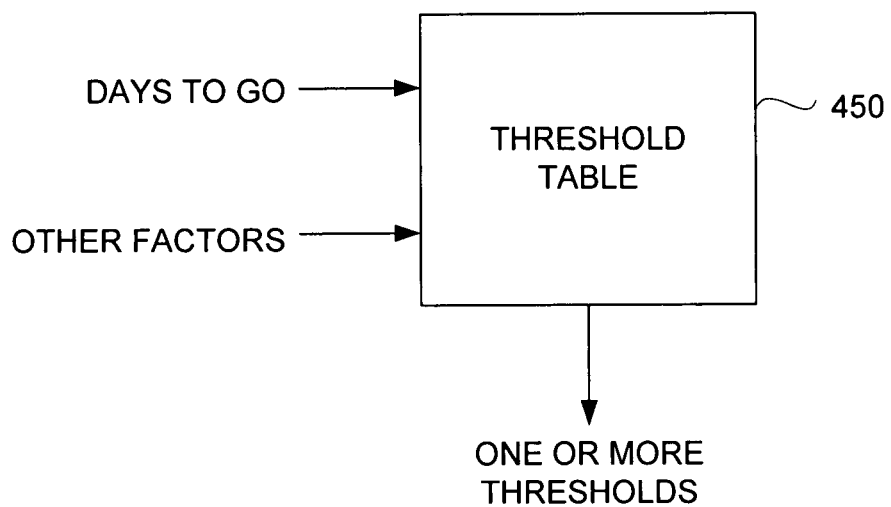
FIG. 4B is a block diagram of a threshold table according to another embodiment of the invention.

FIG. 4B is a block diagram of a threshold table 450 according to another embodiment of the invention. The threshold table 450 receives as inputs a number of days to go as well as one or more other factors. The one or more other factors can pertain to the user characteristics (e.g., user weight, user current/historical activity level, user current/historical health condition, etc.) and/or information from another electronic device. The another electronic device can, for example, use one or more of: temperature sensor, environmental sensor, altitude sensor, humidity sensor, or air quality sensor. The user characteristics can pertain to one or more of weight, age, health, or physical condition. The threshold table 450 can then output one or more thresholds that can be utilized in providing activity feedback to the user. In this embodiment, the one or more thresholds can be dependent upon not only the number of days to go, but also the one or more other factors.

Figure 5A:
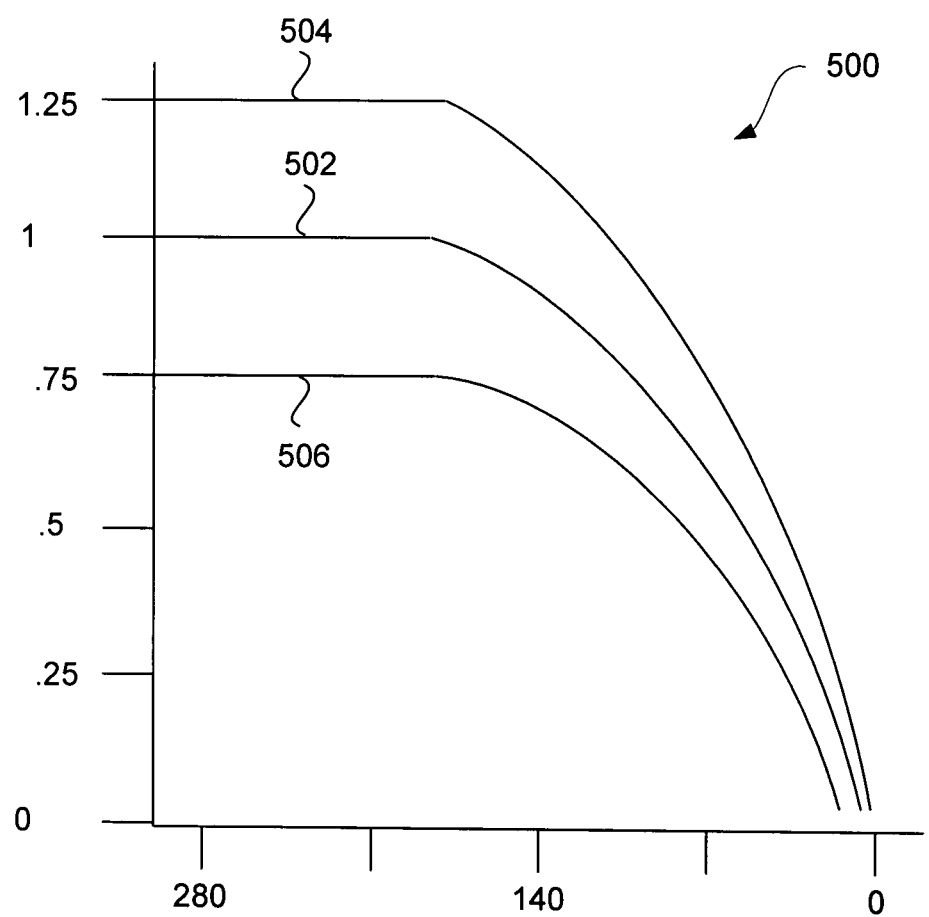
FIG. 5A is an activity threshold graph according to one embodiment of the invention.
Figure 5B:
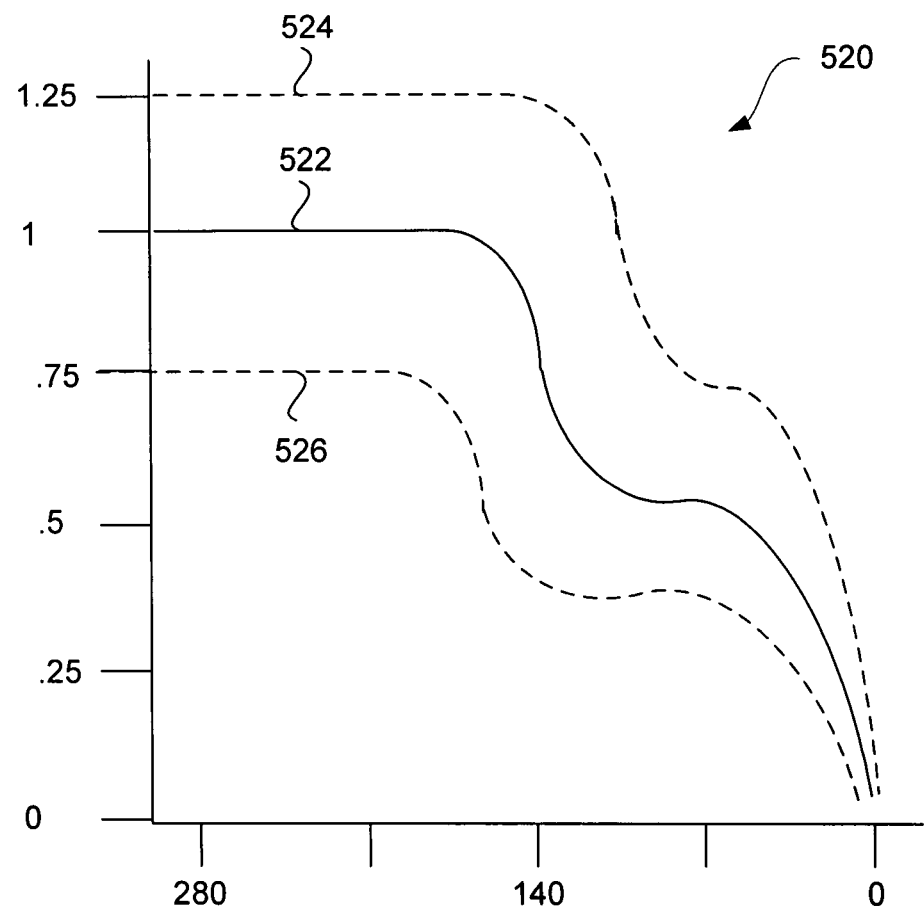
FIG. 5B is an activity threshold graph according to another embodiment of the invention.
Figure 5C:
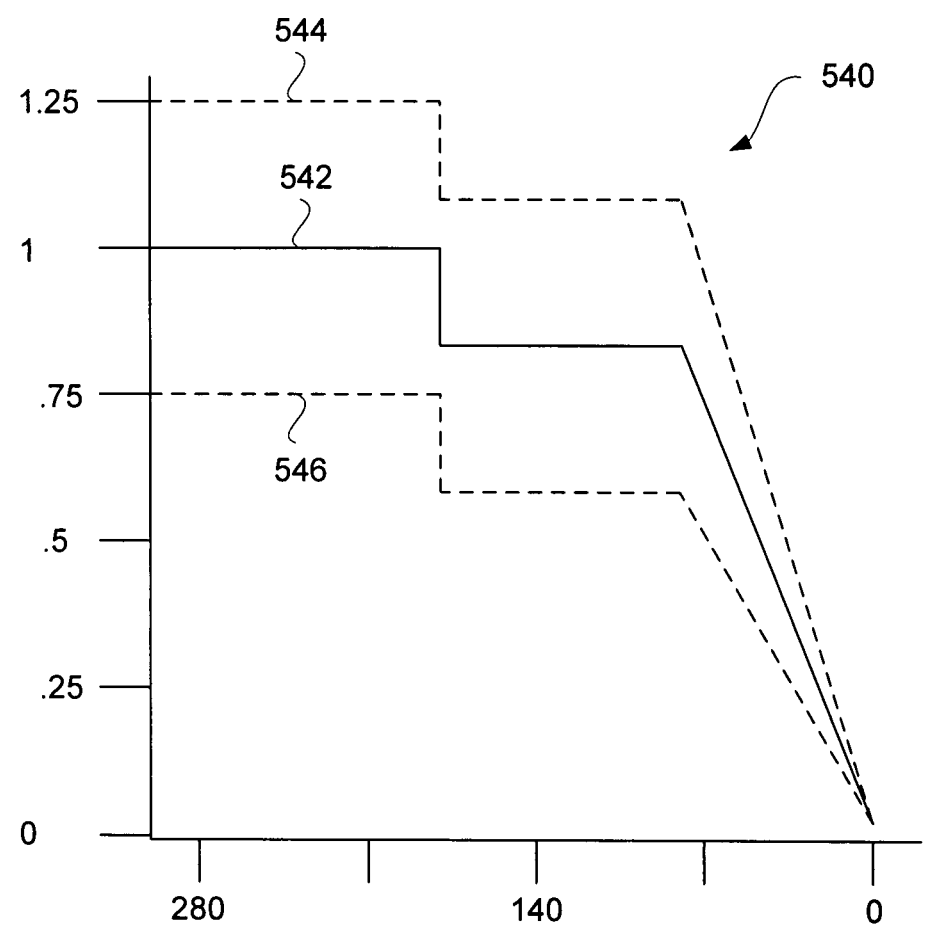
FIG. 5C is an activity threshold graph according to still another embodiment of the invention.

FIGS. 5A-5C are exemplary graphs suitable for provided appropriate threshold levels for an activity monitoring system (e.g., wearable electronic device). The threshold levels can, for example, be dependent on a due date. However, it should be recognized that other dependencies are possible.

FIG. 5A is an activity threshold graph 500 according to one embodiment of the invention. The activity threshold graph 500 illustrates a target activity 502, an upper threshold 504 and a lower threshold 506 according to one exemplary implementation. The vertical axis pertains to an activity level, which has been normalized to the user, such that the activity level of "1" is the target activity level at the beginning of pregnancy. The horizontal axis pertains to a number of days to go. The general trend of the target activity 502 and the thresholds 504 and 506 is that they decrease as the number of days to go decreases. For example, at about 200 days to go, the upper threshold 504 and the lower threshold 506 can begin a gradual decrease over the remaining 200 days to go. In this embodiment, the target activity level can be generally stable at one's normal activity level during the first trimester (e.g., first 100 days) but thereafter gradually decreases until delivery. For example, at about 75 days to go, the target activity level can be decreased to approximately 50% of the activity level at the beginning of pregnancy. Further, at about 25 days to go, the target activity level can be decreased to approximately 25% of the activity level at the beginning of pregnancy. The upper threshold 504 and the lower threshold 546 have also been dramatically lowered when the number of days to go is within this range.

FIG. 5B is an activity threshold graph 520 according to another embodiment of the invention. The activity threshold graph 520 illustrates a target activity 522, an upper threshold 524 and a lower threshold 526 according to one exemplary implementation. The vertical axis pertains to an activity level, which has been normalized to the user, such that the activity level of "1" is the target activity level at the beginning of pregnancy. The horizontal axis pertains to a number of days to go. The general trend of the target activity 522 and the thresholds 524 and 526 is that they decrease as the number of days to go decreases. For example, from about 175 days to go to 105 days to go, the target activity 522 decreases in value by about 50%. Further, at about 25 days to go, the target activity level can be decreased to approximately 25% of the activity level at the beginning of pregnancy. The upper threshold 524 and the lower threshold 526 have also been dramatically lowered when the number of days to go is within this range.

FIG. 5C is an activity threshold graph 540 according to still another embodiment of the invention. The activity threshold graph 540 illustrates a target activity 542, an upper threshold 544 and a lower threshold 546 according to one exemplary implementation. The vertical axis pertains to an activity level, which has been normalized to the user, such that the activity level of "1" is the target activity level at the beginning of pregnancy. The horizontal axis pertains to a number of days to go. The general trend of the target activity 542 and the thresholds 544 and 546 is that they decrease as the number of days to go decreases. For example, at about 200 days to go, the upper threshold 544 and the lower threshold 546 can be decreased such that the target activity level is about 80% of its value at the beginning of pregnancy. As another example, at about 25 days to go, the target activity level can be decreased to approximately 25% of the activity level at the beginning of pregnancy. The upper threshold 544 and the lower threshold 546 have also been dramatically lowered when the number of days to go is within this range. Further, as shown in FIG. 5C, level of the target activity 542 (and thus the thresholds 544 and 546) can further drop off as the number of days to go falls below 25 days.

Besides activity, the wearable electronic device can monitor, track or store other data beyond activity data. In one embodiment, the other data can pertain to one or more of: weight (e.g., user and/or fetus), size (e.g., user and/or fetus), doctors (e.g., contact information), appointments (e.g., doctor appointments), food consumption (e.g., food items, calories, fat content, vitamin content, etc.), nutrition supplement consumption, vitamin consumption, baby information (e.g., baby names), wish list (e.g., baby registry), health information, child health information, child raising information, and the like. Such other data can be provided to the wearable electronic device by a user input mechanism of the wearable electronic device or by electronic transmission (wired or wireless) from another electronic device (e.g., computing device) to the wearable electronic device. In some cases, some or all of the other data can be pre-stored within the portable electronic device. Once such data is stored in the wearable electronic device, the data can be accessed and presented to a user or other interested party. Typically, in one embodiment, a graphical user interface will be provided so that the user can navigate the various types of data and have the particular data of interest presented, such as to an interested party. In another embodiment, the device itself can initiate presentation of certain of the data. For example, the device might daily present (e.g., display) a piece of information of interest to a pregnant woman.

Figure 6A:
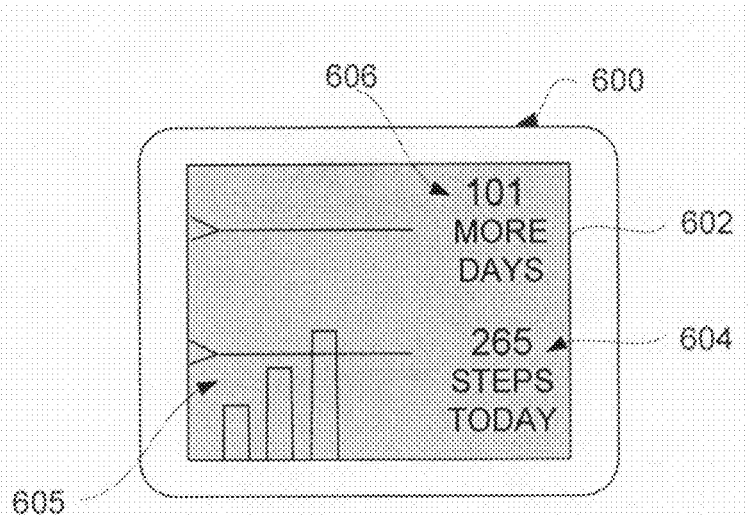
FIG. 6A is a diagram of a wearable electronic device according to one embodiment of the invention.

FIG. 6A is a diagram of a wearable electronic device 600 according to one embodiment of the invention. The wearable electronic device 600 has a housing that supports a display 602. When the wearable electronic device 600 is operational, the display 602 can present a graphical user interface to the user of the wearable electronic device 600. In the embodiment illustrated in FIG. 6A, the graphical user interface being presented on the display 602 indicates (i) a number of steps 604 that the user has taken today, and (ii) a graph 605 indicating activity level of the user as compared to one or more threshold levels. In this example, the graph 605 is a bar graph. Also, in this example, the number of steps 604 the user has taken is "265". The graphical user interface can also present the number of days to go 606 on the display 602. In this example, the number of days to go 606 is "101" days.

Figure 6B:
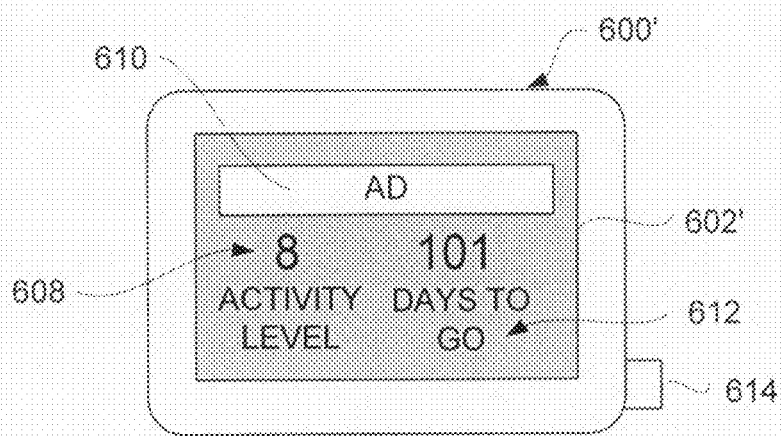
FIG. 6B is a diagram of a wearable electronic device according to another embodiment of the invention.

FIG. 6B illustrates a wearable electronic device 600' according to one embodiment of the invention. The wearable electronic device 600' is generally similar to the wearable electronic device 600 illustrated in FIG. 6A. The wearable electronic device 600' includes a display 602'. The display 602' presents a graphical user interface to the user of the wearable electronic device 600'. The graphical user interface in this embodiment includes a numeric indication of activity level 608, an advertisement 610, and a number of days to go 612. In this example, the activity level 608 is expressed by the number "8", which in this embodiment represents an activity level of "8" out of a maximum "10". The advertisement 610 can be a graphical advertisement, an animated advertisement, etc. The wearable electronic device 600' also includes an input mechanism 614. In one embodiment, the input mechanism 614 is a switch that can provide multiple functions. For example, the switch 614 can be an on, mode and off switch. When the wearable electronic device 600' is off, the switch 614 can serve as an on switch. The switch 614 can operate as an off switch to turn off the wearable electronic device 600' by use of a press and hold operation with the switch 614. When the wearable electronic device 600' is on, the switch 614 can be pressed to switch mode, such as switching between different graphical user interface modes. In FIG. 6B, the input mechanism 614 protrudes from the wearable electronic device 600'. In another embodiment, the input mechanism need not protrude outward from the wearable electronic device 600'. For example, the input mechanism can be located within a recessed area, so that its top surface at least slightly recedes from the surface of the housing of the wearable electronic device 600'.

The content for the advertisement 610 can be stored locally within the wearable electronic device 600'. The content for the advertisement 610 can be pre-stored in the wearable electronic device 600' or electronically transferred to the wearable electronic device 600'. The particular advertisement 610 being displayed can vary depending upon conditions associated with the wearable electronic device 600'. For example, the advertisements can depend upon the number of days to go. To illustrate, during the initial stages of pregnancy, the advertisements can solicit users to purchase books, services and the like for the pregnant user. Towards the end of the pregnancy, the advertisements could reflect products and services for babies.

Figure 6C:
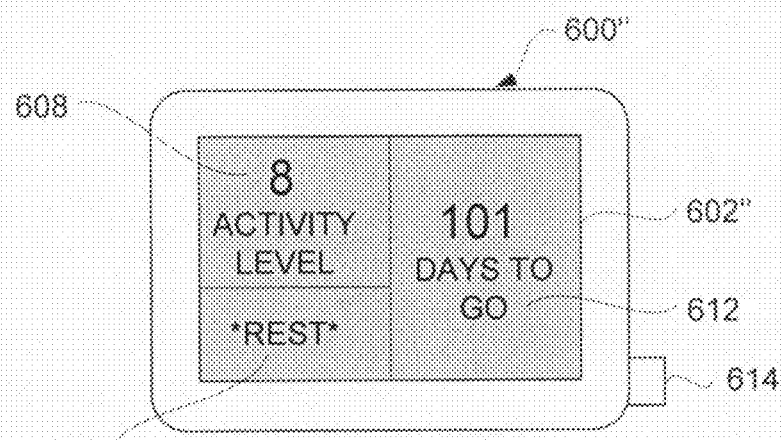
FIG. 6C is a diagram of a wearable electronic device according to one embodiment of the invention.

FIG. 6C is a diagram of a wearable electronic device 600" according to still another embodiment of the invention. The wearable electronic device 600" is generally similar to the wearable electronic device 600' illustrated in FIG. 6B. However, in this embodiment, the graphical user interface being presented on the display 602" includes a numeric activity level 608, a number of days to go 612 and a recommendation 618. The recommendation 618 is provided for the user of the wearable electronic device. For example, as illustrated in FIG. 6C, if the user has undergone an amount of activity during a given day that is approaching an excessive amount, then the graphical user interface can provide a recommendation 618 to the user to rest.

As another example, the recommendation can encourage or remind user not to be stationary for too long during one's pregnancy. If a pregnant woman does not remain sufficiently active, there can be undesired health issues. For example, when a pregnant woman is stationary for too long of a duration, the lack of activity can lead to reduced circulation, swollen legs, back aches, etc. Exercise during pregnancy can, however, serve to allow a woman to improve circulation and avoid swollen legs and back aches. Hence, as an example, the recommendation being displayed, such as the recommendation 618, can alternatively recommend to the user to walk (or otherwise be more active).

In one embodiment, a wearable electronic device can constantly monitor the level of activity of the user. If the user has stayed substantially at the same place for more than a preset period of time, the device can recommend that the user should take a walk. For example, if the user has been stationary for more than 20 minutes, the device would suggest the user to walk 100 steps. The recommendation can be audio or visual. As another example, if the user has not walked more than a predetermined number of steps in a given day, close to the end of the day, the device could prompt the user and indicate to the user a number of steps that she should take before going to sleep. The accumulation (of steps or other activity indicia) can be by day or by week. For example, by Friday of a given week, if the user has not exercised more than a certain amount that week, the device would suggest the user to exercise by a certain amount during the upcoming weekend.

According to one embodiment of the invention, a wearable electronic device can provide a recommendation (or suggestion) for the user of the wearable electronic device. The recommendation can be selected from a plurality of pre-stored recommendations and presented to the user. The recommendation can be selected based on activity level and/or other factors. The recommendation can then, for example, be presented in a graphical user interface, such as the recommendation 618 illustrated in FIG. 6C.

Figure 7A:
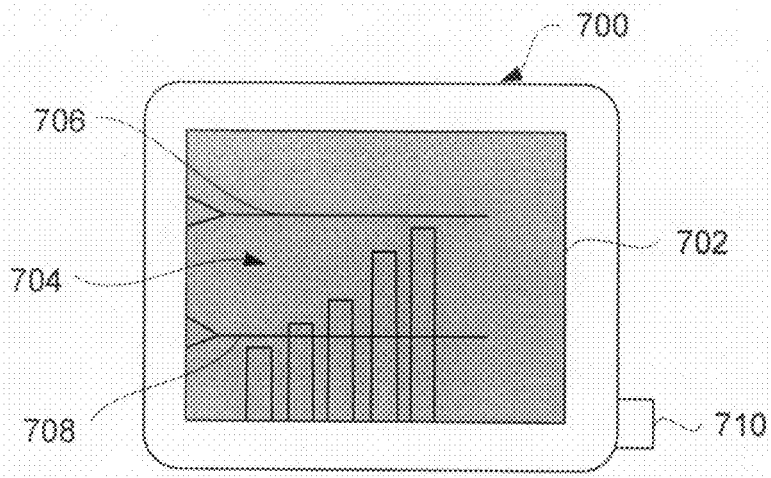
FIG. 7A is a diagram of a wearable electronic device according to one embodiment of the invention.
Figure 7B:
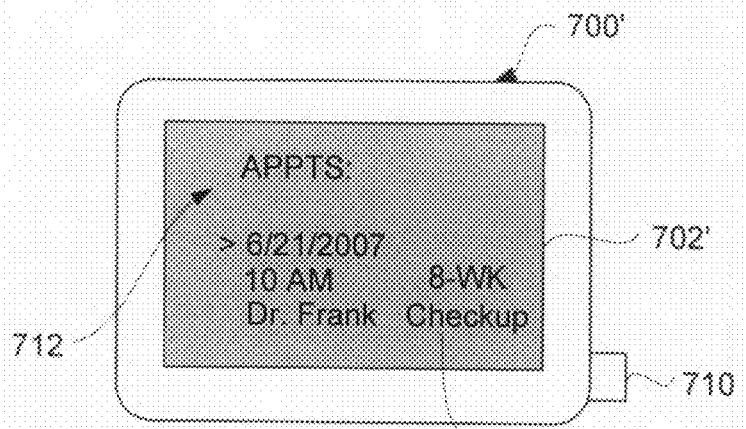
FIG. 7B is a diagram of a wearable electronic device according to another embodiment of the invention.
Figure 7C:
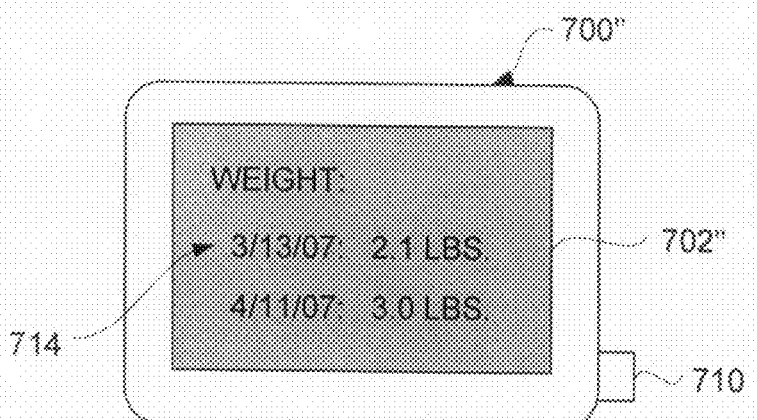
FIG. 7C is a diagram of a wearable electronic device according to still another embodiment of the invention.

A display device of a wearable electronic device can, according to one embodiment, present different output content, such as through different output modes. FIGS. 7A-7C are illustrations of exemplary display modes that can be supported by a wearable electronic device.

FIG. 7A is a diagram of a wearable electronic device 700 according to one embodiment of the invention. The wearable electronic device 700 includes a housing that supports a display 702. As illustrated in FIG. 7A, the display 702 can present a graph 704. The graph 704 provides activity level feedback to the user. In this example, the graph 704 is a bar graph illustrating the activity level for the user. The graph 704 also provides a number of threshold level references 706 and 708. In addition, the wearable electronic device 700 includes an input mechanism 710. In one embodiment, the input mechanism 710 is a switch that can provide multiple functions. For example, similar to the switch 614, the switch 710 can be an on, mode and off switch. The activity level being illustrated by the graph 704 can pertain to a period of time, such as one day, one week or one month.

In another embodiment, a memory of a wearable electronic device can store historical activity information pertaining to the user. In such case, a graph presenting historical data for the user's activity level can be displayed by a display.

FIG. 7B is a diagram of a wearable electronic device 700' according to another embodiment of the invention. The wearable electronic device 700' is generally similar to the wearable electronic device 700 illustrated in FIG. 7A. However, the switch 710 can be activated to switch from the activity feedback graph illustrated in FIG. 7A to a display 702' that presents information on at least one appointment 712 and a short description 713 therefor, as illustrated in FIG. 7B. With the display 702', the user can review appointments and/or enter additional appointments through use of the input mechanism 710. For example, the appointments can be for doctor visits, lab testing visits, etc. The appointments can be recommended appointment times or can be actually scheduled appointments with the service providers. As an example, the appointments can be automatically calculated and tracked by the wearable electronic device (or a computing device coupled thereto) based on a predetermined schedule from date of pregnancy (or due date, or weeks of gestation).

To assist the user with inputting data, the wearable electronic device 700' could also present a virtual keypad or keyboard on the display 702'. Still further, in another embodiment, the wearable electronic device could couple to a computing device from which the user can enter data, such as appointments, that can be transmitted wired or wirelessly to the wearable electronic device 700'. Besides user input, the wearable electronic device can also receive or pre-store other data, such as advertisements, recommendations, and appointments.

FIG. 7C is a diagram of a wearable electronic device 700" according to still another embodiment of the invention. The wearable electronic device 700" is generally similar to the wearable electronic device 700' illustrated in FIG. 7B. However, the wearable electronic device 700" includes a housing that presents a display 702". The display 702" presents a graphical user interface that contains weight information 714 pertaining to the fetus or baby. In this example, as illustrated in FIG. 7C, the weight information 714 provides historical and/or typical weight for the fetus or baby during different phases of pregnancy. Alternatively or additionally, the weight information 714 can pertain to the user (namely, the pregnant woman). The weight information can be used to display a weight progression for the user or for the fetus/baby. For example, the weight information can be presented as interval or cumulative weight gain for the user or the fetus/baby. The interval weight gain can be presented on a monthly basis, such as weight increase during the preceding month (e.g., pounds/month). As an example, the user can input her current weight at any time, and the wearable electronic device can compare the user's actual weight verses an ideal weight as the pregnancy continues. Based on the comparison, the wearable electronic device can present weight information to the user via text, graphics or audio.

Since the weight of the fetus/baby is not as readily available as is the weight of the user, estimation or predictive approaches can be used to approximate the weight of the baby/fetus. In one embodiment, the wearable electronic device can 700" can automatically perform such estimation or predictive approaches. For example, a medical practitioner can utilize one or more measurements of the fetus to estimate the weight of the fetus. The measurements can include one or more of (i) biparietal diameter (e.g., the skull diameter); (ii) femur length (e.g., the length of the thigh); (iii) abdominal circumference; and (iv) crown-rump length (e.g., the height/length of the fetus). To get a better estimate of the weight of the fetus, these measurements can be used together. If the user (i.e., mother) sees a medical practitioner (e.g., doctor) for an ultrasound exam, the medical practitioner can make a better estimate of the baby's weight, and that data can be entered into the wearable electronic device to provide a basis for better future estimates of fetus weight. In another embodiment, the weight of the fetus can be estimated, based on the number of days left in the pregnancy.

Further, any of the graphical user interfaces could also display one or more names selected or proposed for the baby.

In one embodiment, the wearable electronic device can be calibrated for greater accuracy in monitoring activity data. For example, the user can be asked to perform a known activity (while wearing the wearable electronic device that monitors activity data) and then signal the wearable electronic device when the known activity has been completed. The wearable electronic device can then calibrate itself to correct for any difference between the known activity and the monitored activity. The known activity can vary with implementation. For example, the known activity can pertain to walking a predetermined distance. As another example, the known activity can pertain to taking a predetermined number of steps.

Since users tend to have different levels of exercise when they are not pregnant, once pregnant these users will still likely have different exercise levels. In one embodiment, the use of high and low threshold levels can accommodate such variances. In another embodiment, the wearable electronic device can be adapted (e.g., personalized or customized) to a user. For example, a graphical user interface can enable a user to inform the wearable electronic device about her activity level. For example, the wearable electronic device can ask the user one or more questions about her normal amount of activity, i.e., her activity level. As another example, the user can be asked to directly provide an activity indication, e.g., a fitness indication. From the responses to the questions, the wearable electronic device can determine an appropriate activity level suitable for the user. Alternatively, the wearable electronic device can monitor the activity of the user for a duration of time, and automatically determine an activity indication, e.g., a fitness indication. For example, this duration of time can be during the initial phase of pregnancy. In any case, the adaptation, personalization or customization can, for example, alter the target activity and/or threshold levels for the user.

Although the above-described aspect of the invention pertains to an activity feedback system (e.g., wearable electronic device) that is able to assist a pregnant woman during pregnancy, the activity feedback system can also assist the woman after giving birth to a child. For example, a woman's tendons can be prone to injury if excessive activity is resumed too soon after pregnancy. Hence, according to one embodiment, the activity feedback system can be used post-pregnancy to monitor the activity of the woman. As an example, the monitoring can guide the woman to moderate her activity after pregnancy and gradually permit her to return to a normal activity level. For example, the threshold levels and/or recommendations can be used to restrict the woman's activity level for approximately six (6) weeks after pregnancy. The degree of restriction can vary as a function of time. For example, the mother should not walk more than a first number of steps daily during the first week after delivery, and should not walk more than a second number of steps daily six weeks later, with the appropriate number of steps per day increasing (e.g., linearly) as a function of time between week one and week six.

Further, an activity feedback system (e.g., the wearable electronic device) can also interact or be utilized with other electronic devices, which can provide additional information to its user. For example, the activity feedback system can interact with one or more other electronic devices to provide user data or baby data. The user data or baby data can be analyzed, and user or baby information can be made available for output by the other electronic devices. Examples of such other electronic devices are provided in U.S. Provisional Patent Application No. 60/880,308, filed Jan. 12, 2007, and entitled "PORTABLE PRESSURE SENSOR AND HEART-BEAT SENSOR FOR PREGNANCY", which is hereby incorporated herein by reference. As another example, the one or more other electronic devices can also provide information to the activity feedback system. For example, the activity feedback system can interact with one or more other electronic devices to receive user data or baby data from the one or more other electronic devices. The user data or baby data can be analyzed, and user or baby information can be made available for output by the activity feedback system. The connection between the activity feedback system and the other electronic devices can be done wired or wirelessly.

To illustrate, if another electronic device, such as a sensor as described in U.S. Provisional Patent Application No. 60/880,308, indicates that the likelihood for a pre-term baby is high, the activity feedback system can suggest that the user reduce exercise or even suggest bed rest (e.g., extended bed rest). As another example, the another electronic device can be a heart-beat monitor that monitors the user's heart beat. A pregnant woman can faint if her heart beat exceeds 150 beats/minute. Based on the monitored heart beat, the activity feedback system can suggest that the user reduce her level of exercise.

Examples of other information from medical systems that can be used with an activity feedback system as described herein can include, for example, U.S. patent application Ser. No. 11/451,780, filed Jun. 12, 2006 and entitled "HEALTHCASE BASE", now U.S. Patent Publication 2006-0241355-A1, which is hereby incorporated herein by reference.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

Certain aspects of the invention can be implemented in software, hardware or a combination of hardware and software. Certain aspects of the invention can also be embodied as computer readable code on a computer readable medium. The computer readable medium is any data storage device that can store data (e.g., computer program code) which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

In the foregoing description, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

The many features and advantages of the present invention are apparent from the written description. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A wearable electronic device, comprising:
    a housing;
    an activity monitor configured to monitor activity of a user of said wearable electronic device;
    a memory device configured to store information related to the activity of the user and a due date associated with the user;
    a processor operatively connected to said activity monitor and said memory device, said processor being configured to compare information related to the activity of the user with at least one threshold level, wherein the processor is configured to determine the at least one threshold level being dependent on (i) the due date associated with the user, (ii) a user characteristic pertaining to the user, and (iii) calibration information associated with the user, the calibration information being determined based on data acquired from monitoring a predetermined activity of the user while wearing said wearable electronic device; and
    an output device operatively connected to said processor, said output device being configured to output at least activity output information for the user of said wearable electronic device, the activity output information being based at least in part on the comparing of the information related to the activity of the user with the at least one threshold level,
    wherein at least said processor and said memory device are included within said housing, and
    wherein said housing, said activity monitor and said output device of said wearable electronic device are wearable.

2. A wearable electronic device as recited in claim 1, wherein said memory device stores a plurality of threshold levels.

3. A wearable electronic device as recited in claim 2, wherein at least one of the plurality of threshold levels is for use prior to the due date, and wherein at least one of the plurality of threshold levels is for use after the due date.

4. A wearable electronic device as recited in claim 2, wherein the predetermined activity of the user is walking.

5. A wearable electronic device as recited in claim 2, wherein said processor is further configured to determine the one of the threshold levels to be used for comparison with the activity of the user based on a doctor's input associated with the user.

6. A wearable electronic device as recited in claim 2, wherein said memory device is further configured to store at least one weight of the user.

7. A wearable electronic device as recited in claim 1, wherein said processor is configured to determine a number of days until the due date, and causes said output device to output the number of days until the due date.

8. A wearable electronic device as recited in claim 1, wherein said output device is a display.

9. A wearable electronic device as recited in claim 1, wherein said wearable electronic device further comprises:
    a battery for providing power to said wearable electronic device.

10. A wearable electronic device as recited in claim 1, wherein said memory device is further configured to store weight progression of the user during a usage period.

11. A wearable electronic device as recited in claim 1, wherein said memory device is further configured to store historical activity information of the user.

12. A wearable electronic device as recited in claim 1, wherein said memory device is further configured to store at least one advertisement, and
    wherein said processor is further configured to present the at least one advertisement via said output device.

13. A wearable electronic device as recited in claim 1, wherein said memory device is further configured to store a plurality of advertisements, and
    wherein said processor selects one of the advertisements for presentation based on the due date associated with the user and causes the output device to present the selected advertisement.

14. A wearable electronic device as recited in claim 1, wherein said wearable electronic device further comprises at least one input mechanism.

15. A wearable electronic device as recited in claim 14, wherein said input mechanism is configured to receive a user input regarding the due date.

16. A wearable electronic device, comprising:
    a housing that is wearable;
    an activity monitor configured to acquire activity data pertaining to activity of a user of said wearable electronic device;
    a memory device configured to store the activity data and a due date associated with the user;
    a processor operatively connected to said activity monitor and said memory device, said processor being configured to produce activity information based on the activity data and at least one threshold level, the at least one threshold level being dependent on (i) the due date associated with the user and (ii) at least one user characteristic pertaining to the user; and
    an output device operatively connected to said processor, said output device being configured to output the activity information,
    wherein said activity monitor, said memory device, said processor and said output device of said wearable electronic device are provided within said housing which is wearable, and
    wherein said processor determines the at least one threshold level to be used for comparison with the activity data further dependent on calibration information associated with the user, the calibration information being determined on data acquired from monitoring an activity of the user while wearing said wearable electronic device.

* * * * *